United States Patent

Te Koppele et al.

[11] Patent Number: 6,010,863
[45] Date of Patent: Jan. 4, 2000

[54] ASSAY FOR COLLAGEN DEGRADATION

[75] Inventors: Johannes Maria Te Koppele, Leiderdorp; Bob Beekman, Leiden, both of Netherlands

[73] Assignee: Nederlandse Organisatie voor Toegepast-Natuurwetenschappelijk Onderzoek TNO, Netherlands

[21] Appl. No.: 08/931,820

[22] Filed: Sep. 16, 1997

[30] Foreign Application Priority Data

Sep. 17, 1996 [EP] European Pat. Off. ............... 96202596

[51] Int. Cl.[7] ..................................................... G01N 33/53
[52] U.S. Cl. ........................... 435/7.1; 435/7.9; 435/7.92; 435/7.94; 435/975; 436/518; 436/531
[58] Field of Search ........................... 435/7.1, 7.9, 7.92, 435/7.94, 975; 436/518, 531

[56] References Cited

U.S. PATENT DOCUMENTS 5,532,169   7/1996   Eyre ........................................ 436/518

FOREIGN PATENT DOCUMENTS 1287801   8/1991   Canada .

Primary Examiner—Jeffrey Stucker
Attorney, Agent, or Firm—Bachman & LaPointe, P.C.

[57] ABSTRACT

The patent application describes a sandwich-type immunoassay for the detection and/or quantitation of collagen degradation products in biological samples such as blood, serum, plasma, sputum and cell cultures. The immunoassay uses a first antibody directed at an epitope present on a collagen molecule at a distance of up to 165 amino acids from a collagen telopeptide crosslink site, and a second antibody directed at another epitope of the crosslinked collagen molecule.

11 Claims, 8 Drawing Sheets

Fig. 4

N-terminal telopeptide
- α1(I)    QLSYGYDEKSTGGISVP
- α2(I)    QYDGKGVGLGP
- α1(II)   QMAGGFDEKAGGAQLGVMQ
- α1(III)  QNYSPQYDSYDVKSGVAVG triple helical region
1
GPMGPSGPRGLPGPPGAPGPQGFQGPPGEPGEPGASGPMGPRGPPGPPGKNGDDGEAGKPGR
GPMGLMGPRGPPGAAGAPGPQGFQGPAGEPGEPGQTGPAGARGPAGPPGKAGEDGHPGKPGR
GPMGPMGPRGPPGPAGAPGPQGFQGNPGEPGEPGVSGPMGPRGPPGPPGKPGDDGEAGKPGK
GLAGYPGPAGPPGPPGPPGTSGHPGSPGSPGYQGPPGEPGQAGPSGPPGPPGAIGPSGPAGK 63
PGERGPPGPQGARGLPGTAGLPGMKGHRGFSGLDGAKGDAGPAGPKGEPGSPGENGAPGQMG
PGERGVVGPQGARGFPGTPGLPGFKGIRGHNGLDGLKGQPGAPGVKGEPGAPGENGTPGQTG
AGERGPPGPQGARGFPGTPGLPGVKGHRGYPGLDGAKGEAGAPGVKGESGSPGENGSPGPMG
DGESGRPGRPGERGLPGPPGIKGPAGIPGFPGMKGHRGFDGRNGEKGETGAPGLKGENGLPG 125
PRGLPGERGRPGAPGPAGARGNDGATGAAGPPGPTGPAGPPGFPGAVGAKGEAGPQGPRGSE
ARGLPGERGRVGAPGPAGARGSDGSVGPVGPAGPNGSAGPPGFPGAPGPKGEIGAVGNAGPT
PRGLPGERGRTGPAGAAGARGNDGQPGPAGPPGPVGPAGGPGFPGAPGAKGEAGPTGARGPE
ENGAPGPMGPRGAPGERGRPGLPGAAGARGNDGARGSDGQPGPPGPPGTAGFPGSPGAKGEV 187
GPQGVRGEPGPPGPAGAAGPAGNPGADGQPGAKGANGAPGIAGAPGFPGARGPSGPQGPGGP
GPAGPRGEVGLPGLSGPVGPPGNPGANGLTGAKGAAGLPGVAGAPGLPGPRGIPGPPGAAGT
GAQGPRGEPGTPGSPGPAGASGNPGTDGIPGAKGSAGAPGIAGAPGFPGPRGPPDPQGATGP
GPAGSPGSNGAPGQRGEPGPQGHAGAQGPPGPPGINGSPGGKGEMGPAGIPGAPGLMGARGP 249
PGPKGNSGEPGAPGSKGDTGAKGEPGPVGVQGPPGPAGEEGKRGARGEPGPTGLPGPPGERG
TGARGLVGEPGPAGSKGESGNKGEPGSAGPQGPPGPSGEEGKRGPNGEAGSAGPPGPPGLRG
LGPKGQTGKPGIAGFKGEQGPKGEPGPAGPQGAPGPAGEEGKRGARGEPGGVGPIGPPGERG
PGPAGANGAPGLRGGAGEPGKNGAKGEPGPRGERGEAGIPGVPGAKGEDGKDGSPGEPGANG 311
GPGSRGFPGADGVAGPKGPAGERGSPGPAGPKGSPGEAGRPGEAGLPGAKGLTGSPGSPGPD
SPGSRGLPGADGRAGVMGPPGSRGASPGPAGVRGPNGDAGRPGEPGLMGPRGLPGSPGNIGPA
APGNRGFPGQDGLAGPKGAPGERGPSGLAGPKGANGDPGRPGEPGLPGARGLTGRPGDAGPQ
LPGAAGERGAPGFRGPAGPNGIPGEKGPAGERGAPGPAGPRGAAGEPGRDGVPGGPGMRGMP 373
GKTGPPGPAGQDGRPGPPGPPGARGQAGVMGFPGPKGAAGEPGKAGERGVPGPPGAVGPAGK
GKEGPVGLPGIDGRPGPIGPVGARGEPGNIGFPGPKGPTGDPGKNGDKGHAGLAGARGAPGP
GKVGPSGAPGEDGRPGPPGPQGARGQPGVMGFPGPKGANGEPGKAGEKGLPGAPGLRGLPGK
GSPGGPGSDGKPGPPGSQGESGRPGPPGPSGPRGQPGVMGFPGPKGNDGAPGKNGERGGPGG 435
DGEAGAQGPPGPAGPAGERGEQGPAGSPGFQGLPGPAGPPGEAGKPGEQGVPGDLGAPGPSG
DGNNGAQGPPGPQGVQGGKGEQGPAGPPGFQGLPGPSGPAGEVGKPGERGLHGEFGLPGPAG
DGETGAEGPPGPAGPAGERGEQGAPGPSGFQGLPGPPGPPGEGGKPGDQGVPGEAGAPGLVG
PGPQGPPGKNGETGPQGPPGPTGPGGDKGDTGPPGPQGLQGLPGTGGPPGENGKPGEPGPKG

Fig. 4

```
497
ARGERGFPGERGVQGPPGPAGPRGANGAPGNDGAKGDAGAPGAPGSQGAPGLQGMPGERGAA
PRGERGPPGESGAAGPTGPIGSRGPSGPPGPDGNKGEPGVVGAVGTAGPSGPSGLPGERGAA
PRGERGFPGERGSPGAQGLQGPRGLPGTPGTDGPKGASGPAGPPGAQGPPGLQGMPGERGAA
DAGAPGAPGGKGDAGAPGERGPPGLAGAPGLRGGAPPGPEGGKGAAGPPGPPGAAGTPGLQ

559
GLPGPKGDRGDAGPKGADGSPGKDGVRGLTGPIGPPGPAGAPGDKGESGPSGPAGPTGARGA
GIPGGKGEKGEPGLRGEIGNPGRDGARGAHGAVGAPGPAGATGDRGEAGAAGPAGPAGPRGS
GIAGPKGDRGDVGEKGPEGAPGKDGGRGLTGPIGPPGPAGANGEKGEVGPPGPAGSAGARGA
GMPGERGGLGSPGPKGDKGEPGGPGADGVPGKDGPRGPTGPIGPPGPAGQPGDKGEGGAPGL

621
PGDRGEPGPPGPAGFAGPPGADGQPGAKGEPGDAGAKGDAGPPGPAGPAGPPGPIGNVGAPG
PGERGEVGPAGPNGFAGPAGAAGQPGAKGERGGKGPKGENGVVGPTGPVGAAGPAGPNGPPG
PGERGETGPPGTSGIAGPPGADGQPGAKGEQGEAGQKGDAGAPGPQGPSGAPGPQGPTGVTG
PGIAGPRGSPGERGETGPPGPAGFPGAPGQNGEPGGKGERGAPGEKGEGGPPGVAGPPGGSG

683
AKGARGSAGPPGATGFPGAAGRVGPPGPSGNAGPPGPPGPAGKEGGKGPRGETGPAGRPGEV
PAGSRGDGGPPGMTGFPGAAGRTGPPGPSGISGPPGPPGPAGKEGLRGPRGDQGPVGRTGEV
PKGARGAQGPPGATGFPGAAGRVGPPGSNGNPGPPGPPGPSGKDGPKGARGDSGPPGRAGEP
PAGPPGPQGVKGERGSPGGPGAAGFPGARGLPGPPGSNGNPGPPGPSGSPGKDGPPGPAGNT

745
GPPGPPGPAGEKGSPGADGPAGAPGTPGPQGIAGQRGVVGLPGQRGERGFPGLPGPSGEPGK
GAVGPPGFAGEKGPSGEAGTAGPPGTPGPQGLLGAPGILGLPGSRGERGLPGVAGAVGEPGP
GLQGPAGPPGEKGEPGDDGPSGAEGPPGPQGLAGQRGIVGLPGQRGERGFPGLPGPSGEPGQ
GAPGSPGVSGPKGDAGQPGEKGSPGAQGPPGAPGPLGIAGITGARGLAGPPGMPGPRGSPGP

807
QGPSGASGERGPPGPMGPPGLAGPPGESGREGAPGAEGSPGRDGSPGAKGDRGETGPAGPPG
LGIAGPPGARGPPGAVGSPGVNGAPGEAGRDGNPGNDGPPGRDGQPGHKGERGYPGNIGPVG
QGAPGASGDRGPPGPVGPPGLTGPAGEPGREGSPGADGPPGRDGAAGVKGDRGETGAVGAPG
QGVKGESGKPGANGLSGERGPPGPQGLPGLAGTAGEPGRDGNPGSDGLPGRDGSPGGKGDRG

869
APGAPGAPGPVGPAGKSGDRGETGPAGPAGPVGPAGARGPAGPQGPRGDKGETGEQGDRGIK
AAGAPGPHGPVGPAGKHGNRGETGPSGPVGPAGAVGPRGPSGPQGIRGDKGEPGEKGPRGLP
APGPPGSPGPAGPTGKQGDRGEAGAQGPMGPSGPAGARGIQGPQGPRGDKGEAGEPGERGLK
ENGSPGAPGAPGHPGPPGPVGPAGKSGDRGESGPAGPAGAPGPAGSRGAPGPQGPRGDKGET

931
GHRGFSGLQGPPGPPGSPGEQGPSGASGPAGPRGPPGSAGAPGKDGLNGLPGPIGPPGPRGR
GFKGHNGLQGLPGIAGHHGDQGAPGSVGPAGPRGPAGPSGPAGKDGRTGHPGTVGPAGIRGP
GHRGFTGLQGLPGPPGPSGDQGASGPAGPSGPRGPPGPVGPSGKDGANGIPGPIGPPGPRGR
GERGAAGIKGHRGFPGNPGAPGSPGPAGQQGAIGSPGPAGPRGPVGPSGPPGKDGTSGHPGP
```

C-terminal telopeptide

```
TGDAGPVGPPGPPGPPGPPGPP  (1014)        SAGFDFSFLPQPPQEKAHDGGRYYRA
QGHQGPAGPPGPPGPLGPLGV   (1013)
SGETGPAGPPGNPGPPGPPGPP  (1014)        GPGIDMSAFAGLGPREKGPDPLQYMRA
IGPPGPRGNRGERGSEGSPGHPGQPGPPGPPGAPGPC (1029)        CGGVGAAAI
                                              *****of CGGVGAPAI
```

Fig. 5

N-terminal telopeptide
    α1(I)    QLSYGYDEKSTGGISVP
    α2(I)    QYDGKGVGLGP
    α1(II)    QMAGGFDEKAGGAQLGVMQ
    α1(III)    QNYSPQYDSYDVKSGVAVG triple helical region
1
GPMGPSGPRGLPGPPGAPGPQGFQGPPGEPGEPGASGPMGPRGPPGPPGKNGDDGEAGKPGR
GPMGLMGPRGPPGAAGAPGPQGFQGPAGEPGEPGQTGPAGARGPAGPPGKAGEDGHPGKPGR
GPMGPMGPRGPPGPAGAPGPQGFQGNPGEPGEPGVSGPMGPRGPPGPPGKPGDDGEAGKPGK
GLAGYPGPAGPPGPPGPPGTSGHPGSPGSPGYQGPPGEPGQAGPSGPPGPPGAIGPSGPAGK 63
PGERGPPGPQGARGLPGTAGLPGMKGHRGFSGLDGAKGDAGPAGPKGEPGSPGENGAPGQMG
PGERGVVGPQGARGFPGTPGLPGFKGIRGHNGLDGLKGQPGAPGVKGEPGAPGENGTPGQTG
AGERGPPGPQGARGFPGTPGLPGVKGHRGYPGLDGAKGEAGAPGVKGESGSPGENGSPGPMG
DGESGRPGRPGERGLPGPPGIKGPAGIPGFPGMKGHRGFDGRNGEKGETGAPGLKGENGLPG 125
PRGLPGERGRPGAPGPAGARGNDGATGAAGPPGPTGPAGPPGFPGAVGAKGEAGPQGPRGSE
ARGLPGERGRVGAPGPAGARGSDGSVGPVGPAGPNGSAGPPGFPGAPGPKGEIGAVGNAGPT
PRGLPGERGRTGPAGAAGARGNDGQPGPAGPPGPVGPAGGPGFPGAPGAKGEAGPTGARGPE
ENGAPGPMGPRGAPGERGRPGLPGAAGARGNDGARGSDGQPGPPGPPGTAGFPGSPGAKGEV 187
GPQGVRGEPGPPGPAGAAGPAGNPGADGQPGAKGANGAPGIAGAPGFPGARGPSGPQGPGGP
GPAGPRGEVGLPGLSGPVGPPGNPGANGLTGAKGAAGLPGVAGAPGLPGPRGIPGPPGAAGT
GAQGPRGEPGTPGSPGPAGASGNPGTDGIPGAKGSAGAPGIAGAPGFPGPRGPPDPQGATGP
GPAGSPGSNGAPGQRGEPGPQGHAGAQGPPGPPGINGSPGGKGEMGPAGIPGAPGLMGARGP 249
PGPKGNSGEPGAPGSKGDTGAKGEPGPVGVQGPPGPAGEEGKRGARGEPGPTGLPGPPGERG
TGARGLVGEPGPAGSKGESGNKGEPGSAGPQGPPGPSGEEGKRGPNGEAGSAGPPGPPGLRG
LGPKGQTGKPGIAGFKGEQGPKGEPGPAGPQGAPGPAGEEGKRGARGEPGGVGPIGPPGERG
PGPAGANGAPGLRGGAGEPGKNGAKGEPGPRGERGEAGIPGVPGAKGEDGKDGSPGEPGANG 311
GPGSRGFPGADGVAGPKGPAGERGSPGPAGPKGSPGEAGRPGEAGLPGAKGLTGSPGSPGPD
SPGSRGLPGADGRAGVMGPPGSRGASGPAGVRGPNGDAGRPGEPGLMGPRGLPGSPGNIGPA
APGNRGFPGQDGLAGPKGAPGERGPSGLAGPKGANGDPGRPGEPGLPGARGLTGRPGDAGPQ
LPGAAGERGAPGFRGPAGPNGIPGEKGPAGERGAPGPAGPRGAAGEPGRDGVPGGPGMRGMP 373
GKTGPPGPAGQDGRPGPPGPPGARGQAGVMGFPGPKGAAGEPGKAGERGVPGPPGAVGPAGK
GKEGPVGLPGIDGRPGPIGPVGARGEPGNIGFPGPKGPTGDPGKNGDKGHAGLAGARGAPGP
GKVGPSGAPGEDGRPGPPGPQGARGQPGVMGFPGPKGANGEPGKAGEKGLPGAPGLRGLPGK
GSPGGPGSDGKPGPPGSQGESGRPGPPGPSGPRGQPGVMGFPGPKGNDGAPGKNGERGGPGG 435
DGEAGAQGPPGPAGPAGERGEQGPAGSPGFQGLPGPAGPPGEAGKPGEQGVPGDLGAPGPSG
DGNNGAQGPPGPQGVQGGKGEQGPAGPPGFQGLPGPSGPAGEVGKPGERGLHGEFGLPGPAG
DGETGAEGPPGPAGPAGERGEQGAPGPSGFQGLPGPPGPPGEGGKPGDQGVPGEAGAPGLVG
PGPQGPPGKNGETGPQGPPGPTGPGGDKGDTGPPGPQGLQGLPGTGGPPGENGKPGEPGPKG

Fig. 5

497
ARGERGFPGERGVQGPPGPAGPRGANGAPGNDGAKGDAGAPGAPGSQGAPGLQGMPGERGAA
PRGERGPPGESGAAGPTGPIGSRGPSGPPGPDGNKGEPGVVGAVGTAGPSGPSGLPGERGAA
PRGERGFPGERGSPGAQGLQGPRGLPGTPGTDGPKGASGPAGPPGAQGPPGLQGMPGERGAA
DAGAPGAPGGKGDAGAPGERGPPGLAGAPGLRGGAGPPGPEGGKGAAGPPGPPGAAGTPGLQ

559
GLPGPKGDRGDAGPKGADGSPGKDGVRGLTGPIGPPGPAGAPGDKGESGPSGPAGPTGARGA
GIPGGKGEKGEPGLRGEIGNPGRDGARGAHGAVGAPGPAGATGDRGEAGAAGPAGPAGPRGS
GIAGPKGDRGDVGEKGPEGAPGKDGGRGLTGPIGPPGPAGANGEKGEVGPPGPAGSAGARGA
GMPGERGGLGSPGKGDKGEPGGPGADGVPGKDGPRGPTGPIGPPGPAGQPGDKGEGGAPGL

621
PGDRGEPGPPGPAGFAGPPGADGQPGAKGEPGDAGAKGDAGPPGPAGPAGPPGPIGNVGAPG
PGERGEVGPAGPNGFAGPAGAAGQPGAKGERGGKGPKGENGVVGPTGPVGAAGPAGPNGPPG
PGERGETGPPGTSGIAGPPGADGQPGAKGEQGEAGQKGDAGAPGPQGPSGAPGPQGPTGVTG
PGIAGPRGSPGERGETGPPGPAGFPGAPGQNGEPGGKGERGAPGEKGEGGPPGVAGPPGGSG

683
AKGARGSAGPPGATGFPGAAGRVGPPGPSGNAGPPGPPGPAGKEGGKGPRGETGPAGRPGEV
PAGSRGDGGPPGMTGFPGAAGRTGPPGPSGISGPPGPPGPAGKEGLRGPRGDQGPVGRTGEV
PKGARGAQGPPGATGFPGAAGRVGPPGSNGNPGPPGPPGPSGKDGPKGARGDSGPPGRAGEP
PAGPPGPQGVKGERGSPGGPGAAGFPGARGLPGPPGSNGNPGPPGPSGSPGKDGPPGAGNT

745
GPPGPPGPAGEKGSPGADGPAGAPGTPGPQGIAGQRGVVGLPGQRGERGFPGLPGPSGEPGK
GAVGPPGFAGEKGPSGEAGTAGPPGTPGPQGLLGAPGILGLPGSRGERGLPGVAGAVGEPGP
GLQGPAGPPGEKGEPGDDGPSGAEGPPGPQGLAGQRGIVGLPGQRGERGFPGLPGPSGEPGQ
GAPGSPGVSGPKGDAGQPGEKGSPGAQGPPGAPGPLGIAGITGARGLAGPPGMPGPRGSPGP

807
QGPSGASGERGPPGPMGPPGLAGPPGESGREGAPGAEGSPGRDGSPGAKGDRGETGPAGPPG
LGIAGPPGARGPPGAVGSPGVNGAPGEAGRDGNPGNDGPPGRDGQPGHKGERGYPGNIGPVG
QGAPGASGDRGPPGPVGPPGLTGPAGEPGREGSPGADGPPGRDGAAGVKGDRGETGAVGAPG
QGVKGESGKPGANGLSGERGPPGPQGLPGLAGTAGEPGRDGNPGSDGLPGRDGSPGGKGDRG

869
APGAPGAPGPVGPAGKSGDRGETGPAGPAGPVGPAGARGPAGPQGPRGDKGETGEQGDRGIK
AAGAPGPHGPVGPAGKHGNRGETGPSGPVGPAGAVGPRGPSGPQGIRGDKGEPGEKGPRGLP
APGPPGSPGPAGPTGKQGDRGEAGAQGPMGPSGPAGARGIQGPQGPRGDKGEAGEPGERGLK
ENGSPGAPGAPGHPGPPGPVGPAGKSGDRGESPGAGPAGAPGPAGSRGAPGPQGPRGDKGET

931
GHRGFSGLQGPPGPPGSPGEQGPSGASGPAGPRGPPGSAGAPGKDGLNGLPGPIGPPGPRGR
GFKGHNGLQGLPGIAGHHGDQGAPGSVGPAGPRGPAGPSGPAGKDGRTGHPGTVGPAGIRGP
GHRGFTGLQGLPGPPGPSGDQGASGPAGPSGPRGPPGPVGPSGKDGANGIPGPIGPPGPRGR
GERGAAGIKGHRGFPGNPGAPGSPGPAGQQGAIGSPGPAGPRGPVGPSGPPGKDGTSGHPGP

C-terminal telopeptide

TGDAGPVGPPGPPGPPGPPGPP (1014)        SAGFDFSFLPQPPQEKAHDGGRYYRA
QGHQGPAGPPGPPGPLGPLGV (1013)
SGETGPAGPPGNPGPPGPPGPP (1014)         GPGIDMSAFAGLGPREKGPDPLQYMRA
IGPPGPRGNRGERGSEGSPGHPGQPGPPGPPGAPGPC (1029)    CGGVGAAAI
                                           ******of CGGVGAPAI

//ASSAY FOR COLLAGEN DEGRADATION

FIELD OF THE INVENTION

The invention relates to a method for detecting collagen degradation. More specifically, it relates to a method for quantitating high molecular weight crosslinked collagen fragments in blood, plasma, serum, sputum or cell cultures.

BACKGROUND

Collagen proteins in connective tissues constitute a three-dimensional network with crosslinks. The crosslinks are formed after deposition of the collagen molecule in the extracellular matrix. Different types of crosslinks between collagen molecules are known. As a result from enzymatic reactions, lysino-norleucine-type difunctional crosslinks, pyridinoline-type trifunctional crosslinks, and pyrrole-type crosslinks are formed. Aberrant degradation of collagen is an indication of disorders of connective tissues. Disorders of bone tissue comprise osteoporosis, Paget's disease, bone tumours, and drug-related bone loss. Disorders of cartilage tissue occur in arthritis (such as osteo-arthritis and rheumatoid arthritis), and disorders of the cardiovascular system are prominent in atherosclerosis, aneurisms, hypertension, myocardial infarction and hypertrophy. Similarly, disorders of the respiratory system and liver, such as fibrosis, of the teeth and periodontal tissues, of skin and wound healing, and in tumours involve changes in collagen turnover.

Known methods to determine turnover of connective tissues, in particular bone, are based on serum/plasma/blood or urinary levels of pyridinoline crosslinks (free or still containing residual amino acids), or telopeptide sequences corresponding to the crosslinking site. For example U.S. Pat. No. 5,140,103 discloses a method for measuring collagen degradation by quantitating the concentration of a C-terminal collagen type II or III telopeptide containing a pyridinoline-type crosslink by immunological, electrochemical or fluorometric assays. WO-92/21698 describes a method of determining bone resorption by means of antibodies to type I collagen telopeptides. WO-95/08115 discloses a method for assaying collagen fragments by means of antibodies against crosslinking sites of collagen. Similarly, WO-91/10141 describes the use of antibodies to detect collagen-derived crosslinks in biological fluids as a diagnostic method of bone diseases.

A disadvantage of these known methods for assaying collagen degradation is that the detection means (e.g. antibodies) recognise an epitope that includes the crosslink, or an epitope close to the crosslinking site. Thus, these methods depend on the nature and structure of the crosslink, or the amino acid sequence close to the crosslinking site. Collagen fragments containing other types of crosslinks are not necessarily detected and thus not quantitated, which leads to a less reliable and/or less sensitive result. More importantly, most of these methods require a relatively insensitive and laborious competition-type immunoassay that is mostly only applicable to urine, and not to serum/plasma/blood. Disadvantages of urinary assays are the need to correct for the urine volume based on creatinine levels, diurnal variation in urinary excretion rate and the need to collect urine samples.

STRUCTURE OF COLLAGEN CROSSLINKING

The formation of crosslinks in collagen is a basic feature of maturation of the tissue. The crosslinks can be intramolecular, linking two collagen α-chains within the same molecule, or intermolecular, between chains in different molecules. Irrespective of the exact structure of the crosslink, by definition they involve two or more α-chains.

The chemistry and biology of crosslink formation have been reviewed extensively. The basic mechanism of crosslinking is oxidative deamination of the α-amino groups of lysine or hydroxylysine residues, catalysed by lysyl oxidase. The lysine or hydroxylysine aldehydes formed undergo condensation reactions with lysine or hydroxylysine into the difunctional crosslinks (dehydro)-lysinonorleucine, -hydroylysinonorleucine, and -dihydroxylysinonorleucine. Other difunctional crosslinks involve aldol condensation of two aldehydes, and pyrrole-type crosslinks.

Subsequently, trifunctional crosslinks connecting three α-chains may result: for instance, hydroxylysinonorleucine and dihydroxylysinonorleucine are converted into the pyridinoline crosslinks lysylpyridinoline (LP) and hydroxylysylpyridinoline (HP), respectively. The difunctional crosslink hydroxylysinonorleucine may also undergo condensation with histidine to form the trifunctional crosslink histidinohydroxylysinonorleucine. Furthermore, the aldol product of two hydroxylysine aldehydes can undergo condensation with hydroxylysine resulting in hydroxymerodesmosine, or with histidine leading to dehydroaldolhistidine. The latter can undergo additional condensation with lysine or hydroxylysine to produce the tetrafunctional crosslinks dehydro-histidino-merodesmosine and dehydro-histidino-hydroxymerodesmosine, respectively.

The type of crosslink formation depends more on tissue localisation than on the type of collagen. For instance, crosslinks based on lysine aldehydes predominate in skin. The crosslinks formed via the hydroxylysine pathway predominate in bone and cartilage. The di-, tri- or tetrafunctional crosslinks are reproducibly located at predefined positions in the collagen molecule, probably due to the selectivity of lysyl oxidase. For instance, difunctional hydroxylysinonorleucine and dihydroxylysinonorleucine and their trifunctional pyridinoline maturation products (LP and HP, respectively) in bone and cartilage (type I and II collagen, respectively) involve the lysine or hydroxylysine at position 87 in the triple helix and the hydroxylysine residue in the C-terminal telopeptide. Furthermore, these crosslinks are formed between lysine or hydroxylysine at position 930 of the triple helix and the hydroxylysine residue in the N-terminal telopeptide (see FIG. 2).

In type II collagen, composed of three identical $α_1(II)$-chains, by definition crosslinks are homotypic. Similarly, crosslinks of type III collagen (composed of three $α_1(III)$-chains) are homotypic. Homotypic crosslinks in type I collagen may involve the $α_1(I)$- as well as the $α_2(I)$-chain. Also heterotypic crosslinliks, connecting different collagen molecules have been reported: crosslinks between type I and III collagen in blood vessels, between type II and IX, type II and IX, and type II and III collagen in cartilage, between type I and V in bone, and between type I and II in intervertebral disc.

In summary, the enzymatic crosslinks are very diverse in nature, occur at specific locations in the molecule, and connect two or more collagen α-chains from the same or different types of collagen (homo- and heterotypic crosslinks).

SUMMARY OF THE INVENTION

It has been found according to the invention that collagen degradation can be measured effectively in plasma, serum or blood by a sandwich-type of immunoassay using epitopes further removed from the crosslinking site. The invention is concerned with a method of assaying collagen degradation products as defined in the appending claims; the method is generally applicable to crosslinked collagen fragments irrespective of the exact nature and structure of the crosslinking site. The invention also pertains to antibodies and diagnostic kits for carrying such a method.

DETAILED DESCRIPTION OF THE INVENTION

It was found by HPLC analysis of normal serum that pyridinoline crosslinks are present in collagen degradation products with relatively high molecular weight (cf. Example 1; FIG. 1). About 25, 50 and 25% have molecular weights between 0-10, 10–30, and 30–50 kD, respectively. Assuming an average weight per amino acid of 100 Dalton, half of the collagen degradation products in serum contain between 100 and 300 amino acids. One quarter of the fragments comprise 300–500 amino acids, while another quarter represents fragments with less than 100 amino acids. This implies that collagen degradation products present in blood can be as large as 500 amino acids. Thus, on average the three α-chains of the pyridinoline crosslink-containing degradation products are as large as up to 500/3=165 amino acids. Thus, these fragments contain not only (part of) the collagen telopeptide (telopeptides usually comprise about 15 amino acids), but also large peptides, up to 165 amino acids, from the triple helical region (FIG. 2).

According to the invention high-molecular weight collagen fragments can be detected by α-chain epitopes residing in the triple helical region, irrespective of the type of crosslink. Inasmuch as two, three or four α-chains are present in these collagen degradation products in serum, a sandwich-type of assay with one antibody recognising an epitope in one α-chain, and a second antibody recognising another α-chain (which may be the same type of α-chain), or even on the same α-chain as explained below, is proposed. The two or more epitopes for the antibodies can be present on the degradation product at different locations as depicted in FIG. 3.

The epitopes suitable for the present method are located at a distance of up to 165 amino acids from a collagen chain crosslink site. A distance of an epitope to a crosslink site of a particular number of amino acids is understood as that number of amino acids along the amino acid chain from the distal amino acid of the epitope to the lysine or hydroxylysine residue of either a telopeptide crosslink site or a triple helical region crosslink site, the latter being located at about 100 amino acids distance from the collagen chain ends (see FIGS. 4 and 5).

An especially preferred distance from the crosslink sites (whether telopeptide or triple helical) is up to 100 amino acids, especially 5–100 or even 10–90 amino acids.

One of the epitopes should be present on a chain having a telopeptide crosslink site. It may be present on the crosslink site itself and even comprise part of the other chains linked by the crosslink. If the first epitope is present on the telopeptide crosslink, the second epitope may reside on the same chain, as depicted in FIG. 3, variations 3 and 5. The second epitope may, however, also be present on another chain (FIG. 3, variations 2, 8 and 9). If the first epitope is at some distance (e.g. >5 amino acids) from the telopeptide crosslink, to the extent that an antibody to the epitope does not discriminate for the presence of the crosslink, the second epitope should be present on another α- chain, in order to selectively detect degradation products that contain a crosslink (FIG. 3, variations 1, 4, 6 and 7). In this case, where the two α-chains are the same, the epitopes may be the same as well (FIG. 3, variation 7). A very suitable combination of epitopes (and antibodies) for the sandwich assay is a first epitope on a collagen within 165 amino acids from a telopeptide crosslink, and a second epitope on another collagen chain within 165 amino acids from a triple helical region crosslink; this combination recognises most of the degradation products that are of diagnostic interest. If the telopeptide crosslink is N-terminal, the helical region crosslink is at the 930 or equivalent position (FIG. 3, variations 1, 2, 4, 9), whereas if the telopeptide crosslink is C-terminal, the helical region crosslink is at the 87 or equivalent position (not depicted in FIG. 3, but similarly applicable).

The antibodies according to the invention can be produced by well-known methods. Preferably the antibodies are monoclonal antibodies generated by immunisation with either natural collagen degradation products having molecular weights of up to 50 kD, or with synthetic peptides containing at least the epitope of interest.

One of said antibodies is preferably immobilised in a known way, e.g. by physical or covalent binding to spheres, beads, sticks, plate walls, and the like, or immobilisable by aspecific reaction with a further, immobilised antibody.

Another of the other of said antibodies is preferably detectable by being provided with a detectable label, such as a fluorescence marker, a radioisotope, an enzyme, an avidine-biotine marker or the like, or by being recognised by a further, labelled antibody.

The invention further provides novel antibodies as described above, directed at an epitope which is at some distance, up to 165 amino acids, in particular 5–150 amino acids, more in particular 10 –100 amino acids, from a crosslink site. The invention also provides a diagnostic kit containing at least one of such antibodies, optionally two of said antibodies, one being immobilised or immobilisable, the other being labelled or detectable. The kit may further contain conventional means for carrying out a sandwich-type immunoassay, such as enzyme substrates in case of enzyme labels, diluents, buffers, filters, etc.

One of the two antibodies drawn in each of the 9 possible situations (panel A) serves as a catching antibody. The other antibody, that may be identical to the first, is used to detect the collagen degradation fragments, by whatever means, in a sandwich assay (see panel B). Antibodies directed against any epitope in situations 1–9 may serve the purpose of developing a sensitive and convenient assay to detect or/and quantitate collagen degradation products in serum, plasma or blood or other medium.

FIG. 4. Sequences of collagen types I, II and III proteins, with possible sites of epitopes based on crosslinking residue in triple helical region. The underlined parts represent epitopes based on crosslinking residues in triple helical region; double underlined are residues involved in lysyl oxidase-mediated crosslinking. P represents proline or hydroxyproline, K represents lysine or hydroxylysine (optionally glycosylated).

FIG. 5: Sequences of collagen types I, II and III proteins, with possible sites of epitopes based on crosslinking residue in telopeptides. The underlined parts represent epitopes based on crosslinking residues in telopeptides; double underlined are residues involved in lysyl oxidase-mediated crosslinking. P represents proline or hydroxyproline, K represents lysine or hydroxylysine (optionally glycosylated).

EXAMPLE 1

Normal human serum was separated into fractions with different molecular weight by ultrafiltration: serum (10 ml) was passed through cut off-filters of 100, 50, 30, and 10 kD (Centriprep, Grace BV, Amicon Division, Capelle aan de IJssel, The Netherlands. Fractions (0.5 ml) with molecular weight of <10 kD, 10–30 , 30–50 kD, and 50–100 kD were dried, reconstituted in 250 μl 6 N HCl, and hydrolysed at 108° C. for 16 hours. Hydrolysed fractions were dried, reconstituted in 500 μl 6N HCl, 200 μl glacial acetic acid, 200 μl CF-1 cellulose slurry, and 800 μl n-butanol, and subjected to solid phase extraction with CF-1 cellulose according to Black et al, (Anal. Biochem. 1988, 169: 197–203). HPLChromatography was used for quantitating amounts of pyridinoline crosslinks, which were detected by their fluoresence at 295/400 nm (excitation/emission wavelengths) (see Black et al. above).

Figure 1:
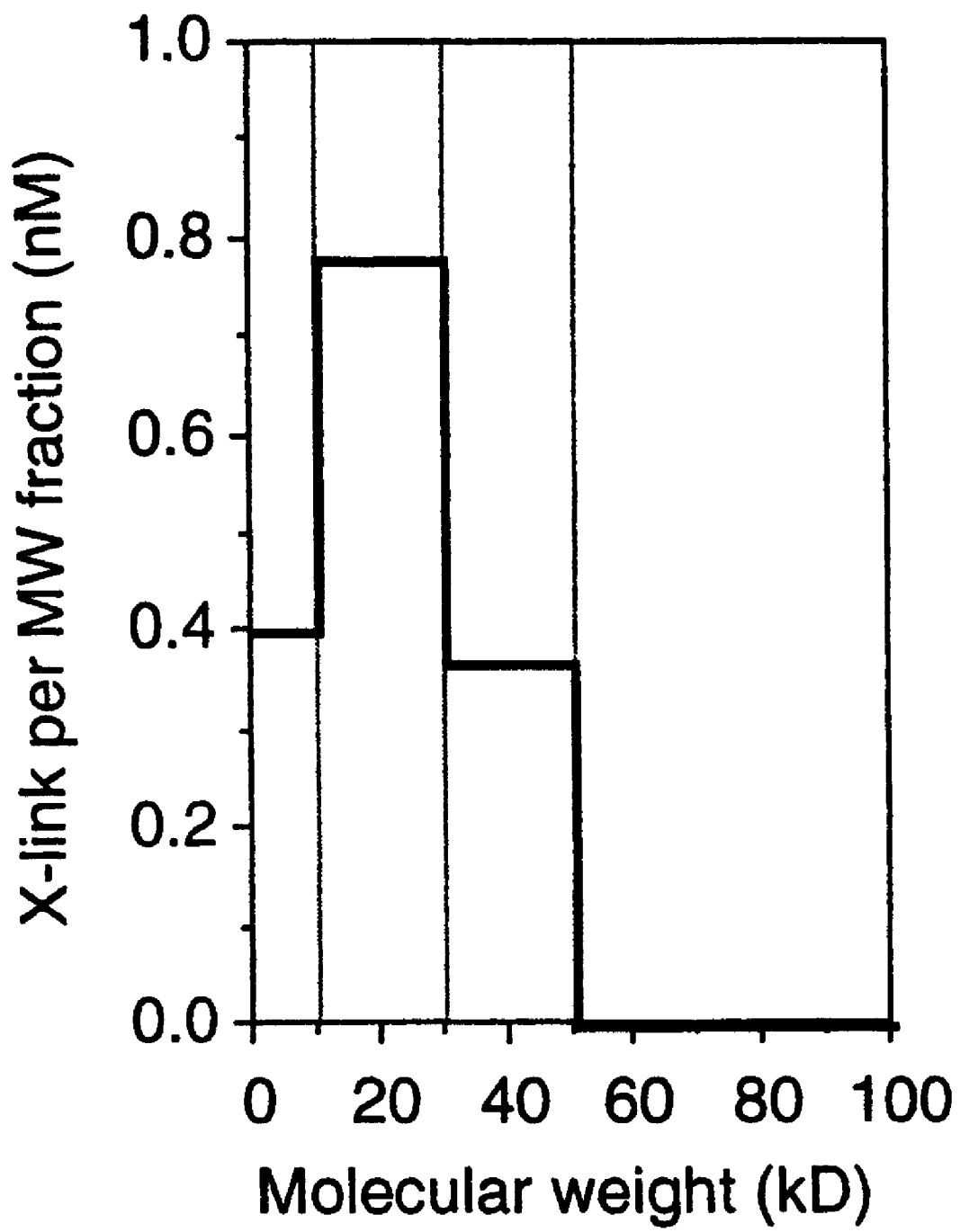
FIG. 1. Molecular weight distribution, on a molar basis, of collagen degradation products containing pyridinoline crosslinks in normal human serum.
Figure 2:
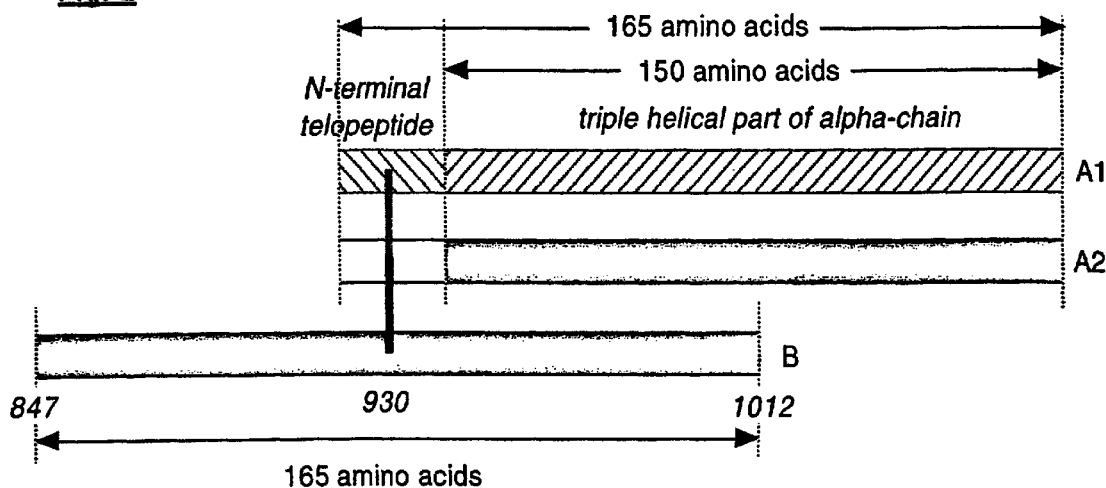
FIG. 2. Schematic representation of collagen degradation products present in serum, based on findings presented in FIG. 1, and illustrated for collagen types I, II and III. Fragments containing trifunctional crosslinks (e.g. pyridinolines) contain all 3 α-chains (A1, A2, and B; C1, C2, and D). Fragments with difunctional crosslinks are composed of 2 α-chains (A2 and B; C2 and D). The maximal length of each peptide chain is on average 165 amino acids (α-chains B and D and A1, A2, C1 and C2 some 15 thereof represent the N- or C-terminal telopeptide; the remaining α-chain of 150 (or less) amino acids α-chain are derived from the triple helical region). Italic numbers refer to residue numbers of the triple helix. Although the triple helix region fragments (B and D are depicted with the crosslink site 930 or 87 in the middle, other fragments are equally possible (e.g. 800–965 in B or and 35–200 in D, or shorter fragments).
Figure 2:
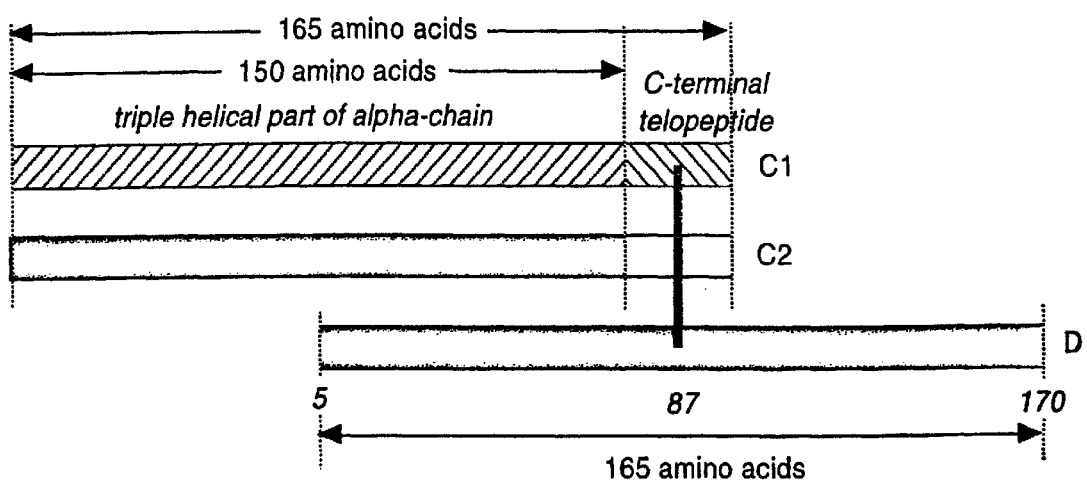
Figure 3:
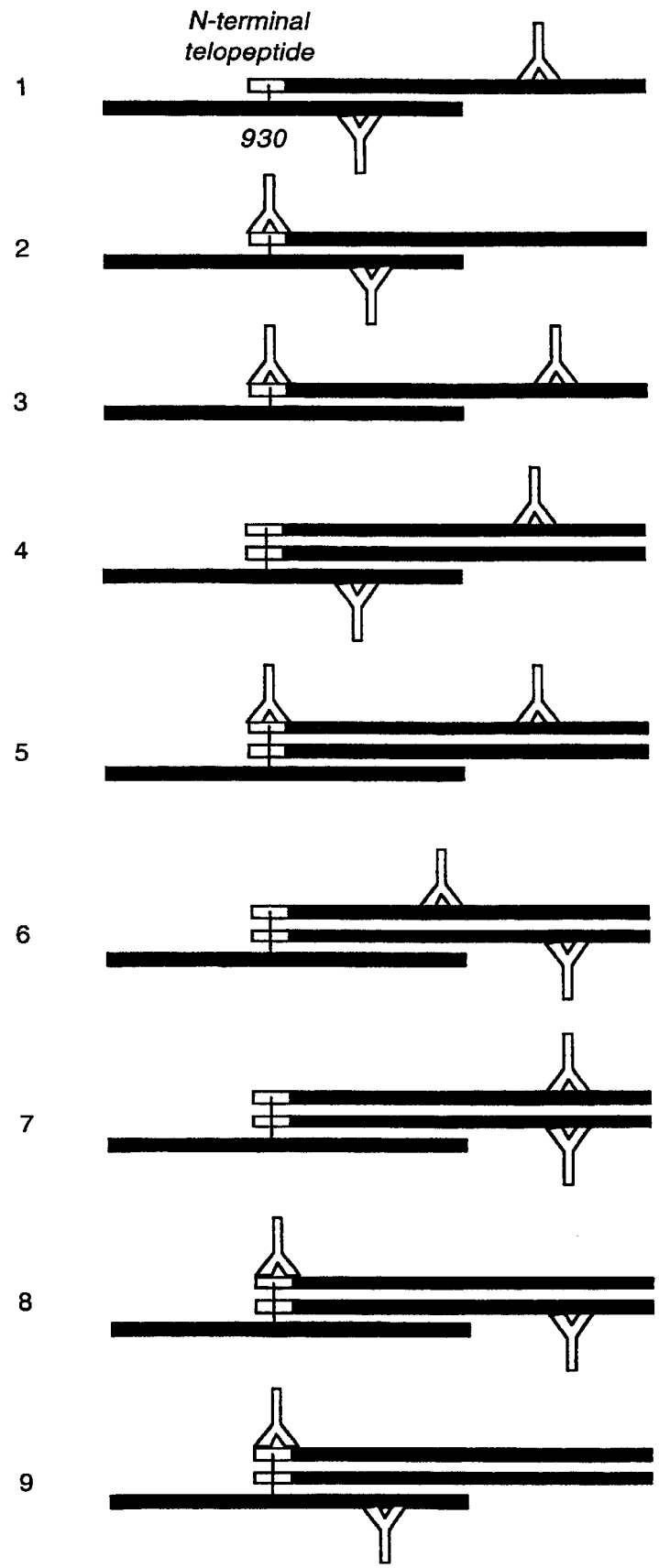
FIG. 3. Principle of sandwich-type assay of high-molecular weight crosslinked collagen degradation products in serum, plasma or blood, illustrated with degradation products composed of two or three α-chains crosslinked at residue 930 of the triple helix and the N-terminal telopeptide, originating from homotypically crosslinked collagens type I, II or III. The antibody recognising the telopeptide (situations 2, 3, 5, 8 and 9) may recognise any of the drawn telopeptides, as well as shared epitopes between two telopeptides, or telopeptide and triple helical region (not depicted). Similar principles apply to the fragments containing crosslinks between residue 87 and the C-terminal telopeptide of these collagens, as well as to heterotypically crosslinked fragments derived from combinations of collagens such as type I and II, I and III, I and V, II and III, II and IX, and II and XI.
Figure 3:
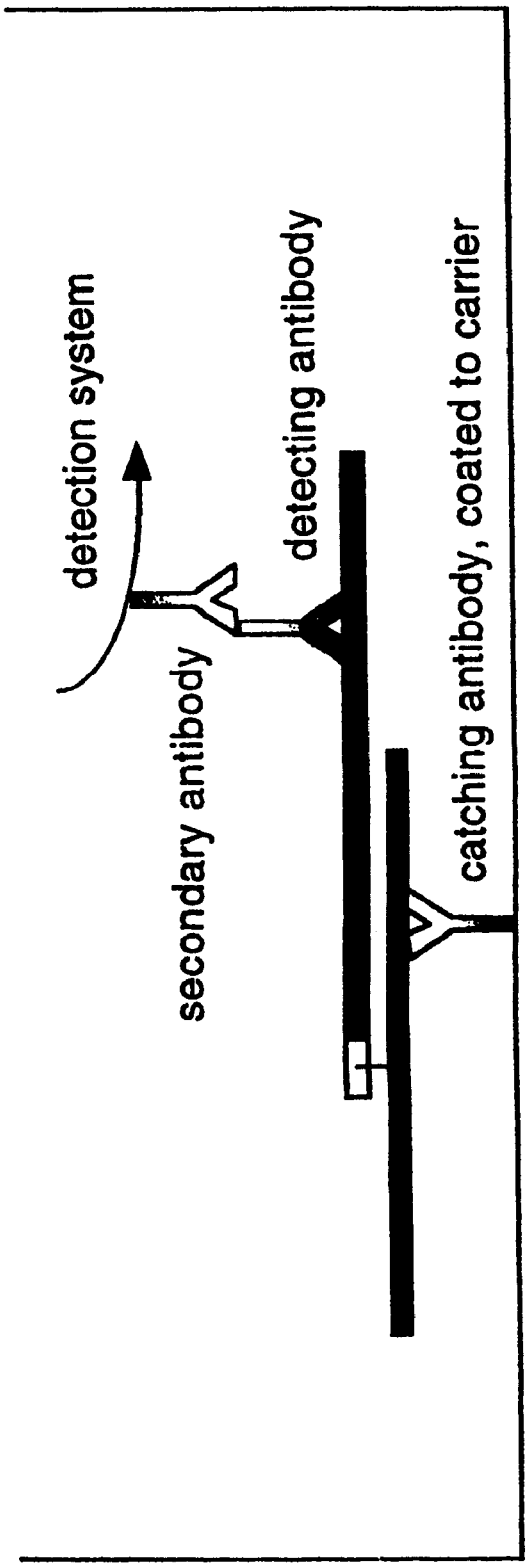

Substantial amounts of pyridinoline crosslinks (the sum of hydroxylysylpyridinoline and lysylpyridinoline) were detected in 0–10, 10–30, and 30–50 kD fractions. About half of the total serum concentration of pyridinoline (approx. 1.5 nM) had a molecular weight between 10 and 30 kD. About 25% had a molecular weight less than 10 kD. The other 25% had molecular weight between 30 and 50 kD (FIG. 1).

What is claim is:

1. Method for assaying collagen degradation by assaying degradation products containing a collagen crosslink in a biological sample other than urine, which comprises (a) contacting said sample, or a fraction thereof containing protein material, with a first antibody directed at a first epitope present on a crosslinked collagen molecule, said first epitope being located at a distance of up to 165 amino acids from a collagen telopeptide crosslink site, and a second antibody directed at a second epitope present on said collagen molecule, said second epitope being located at a distance of up to 165 amino acids from a collagen crosslink site, at least one of said first and second epitopes being located at a distance of at least 5 amino acids from a collagen crosslink site, and (b) detecting a complex formed by said collagen degradation product and said first and said second antibody.

2. Method according to claim 1, wherein one of said antibodies is detectable and the other of said antibodies is immobilised.

3. Method according to claim 1, wherein said second epitope is present on a collagen molecule at a distance of 5 to 150 amino acids from a collagen triple helical region crosslink site.

4. Method according to claim 1, wherein said second epitope is present on a collagen molecule at a distance of 5 to 165 amino acids from a collagen telopeptide crosslink site.

5. Method according to claim 2, for assaying degradation of collagen having at least two identical α-chains, wherein said first antibody and said second antibody are directed at an identical epitope present on said identical α-chains of a collagen molecule at a distance of from 5 to 165 amino acids from a collagen telopeptide crosslink site.

6. Method according to claim 1, wherein said first epitope is present on a collagen telopeptide crosslink site, and said second epitope is present on a collagen molecule at a distance of 5 to 165 amino acids from a collagen crosslink site.

7. Method according to claim 1, wherein at least one of said first and said second epitope is located at a distance of 5 to 100 amino acids from said collagen crosslink site.

8. Method according to claim 1, wherein at least one of said first and said second epitope is present on the collagen α1(I), α2(I), α1(II) or α1(III) chain or an α-chain of collagen type IV, V, VI, IX, X or XI.

9. Method according to claim 1, wherein said protein material has molecular weights between 3 kD and 50 kD, in particular between 5 kD and 40 kD.

10. Method according claim 1, wherein said biological sample is derived from blood, serum, plasma or sputum.

11. Diagnostic kit for assaying bone degradation products containing a collagen crosslink, the kit containing at least first and second antibodies directed at first and second epitopes, respectively, present on a crosslinked collagen molecule, at least one of said antibodies being directed at an epitope located at a distance of up to 165 amino acids from a collagen telopeptide crosslink site, of said collagen molecule, and at least one of said antibodies being directed at an epitope located at a distance of 5 to 165 amino acids from a collagen crosslink site of said collagen molecule.

* * * * *

```
SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
        (A) LENGTH: 1057 amino acids
        (B) TYPE: amino acid
        (C) STRANDEDNESS: single
        (D) TOPOLOGY: linear (ii) MOLECULE TYPE: protein (iii) HYPOTHETICAL: NO (iii) ANTI-SENSE: NO (vi) ORIGINAL SOURCE:
        (A) ORGANISM: Homo sapiens
        (F) TISSUE TYPE: Collagen type I (xi) SEQUENCE DESCRIPTION: SEQ ID NO: 1:

Gln Leu Ser Tyr Gly Tyr Asp Glu Lys Ser Thr Gly Gly Ile Ser Val
 1               5                  10                  15

Pro Gly Pro Met Gly Pro Ser Gly Pro Arg Gly Leu Pro Gly Pro Pro
                20                  25                  30

Gly Ala Pro Gly Pro Gln Gly Phe Gln Gly Pro Pro Gly Glu Pro Gly
            35                  40                  45
```

-continued

```
Glu Pro Gly Ala Ser Gly Pro Met Gly Pro Arg Gly Pro Pro Gly Pro
 50                  55                  60
Pro Gly Lys Asn Gly Asp Asp Gly Glu Ala Gly Lys Pro Gly Arg Pro
 65                  70                  75                  80
Gly Glu Arg Gly Pro Pro Gly Pro Gln Gly Ala Arg Gly Leu Pro Gly
                 85                  90                  95
Thr Ala Gly Leu Pro Gly Met Lys Gly His Arg Gly Phe Ser Gly Leu
                100                 105                 110
Asp Gly Ala Lys Gly Asp Ala Gly Pro Ala Gly Pro Lys Gly Glu Pro
                115                 120                 125
Gly Ser Pro Gly Glu Asn Gly Ala Pro Gly Gln Met Gly Pro Arg Gly
                130                 135                 140
Leu Pro Gly Glu Arg Gly Arg Pro Gly Ala Pro Gly Pro Ala Gly Ala
145                 150                 155                 160
Arg Gly Asn Asp Gly Ala Thr Gly Ala Ala Gly Pro Pro Gly Pro Thr
                165                 170                 175
Gly Pro Ala Gly Pro Pro Gly Phe Pro Gly Ala Val Gly Ala Lys Gly
                180                 185                 190
Glu Ala Gly Pro Gln Gly Pro Arg Gly Ser Glu Gly Pro Gln Gly Val
                195                 200                 205
Arg Gly Glu Pro Gly Pro Pro Gly Pro Ala Gly Ala Ala Gly Pro Ala
210                 215                 220
Gly Asn Pro Gly Ala Asp Gly Gln Pro Gly Ala Lys Gly Ala Asn Gly
225                 230                 235                 240
Ala Pro Gly Ile Ala Gly Ala Pro Gly Phe Pro Gly Ala Arg Gly Pro
                245                 250                 255
Ser Gly Pro Gln Gly Pro Gly Pro Thr Gly Ala Arg Gly Leu Val
                260                 265                 270
Gly Glu Pro Gly Pro Ala Gly Ser Lys Gly Glu Ser Gly Asn Lys Gly
                275                 280                 285
Glu Pro Gly Ser Ala Gly Pro Gln Gly Pro Pro Gly Pro Ser Gly Glu
                290                 295                 300
Glu Gly Lys Arg Gly Pro Asn Gly Glu Ala Gly Ser Ala Gly Pro Pro
305                 310                 315                 320
Gly Pro Pro Gly Leu Arg Gly Gly Pro Gly Ser Arg Gly Phe Pro Gly
                325                 330                 335
Ala Asp Gly Val Ala Gly Pro Lys Gly Pro Ala Gly Glu Arg Gly Ser
                340                 345                 350
Pro Gly Pro Ala Gly Pro Lys Gly Ser Pro Gly Glu Ala Gly Arg Pro
                355                 360                 365
Gly Glu Ala Gly Leu Pro Gly Ala Lys Gly Leu Thr Gly Ser Pro Gly
                370                 375                 380
Ser Pro Gly Pro Asp Gly Lys Thr Gly Pro Pro Gly Pro Ala Gly Gln
385                 390                 395                 400
Asp Gly Arg Pro Gly Pro Pro Gly Pro Pro Gly Ala Arg Gly Gln Ala
                405                 410                 415
Gly Val Met Gly Phe Pro Gly Pro Lys Gly Ala Ala Gly Glu Pro Gly
                420                 425                 430
Lys Ala Gly Glu Arg Gly Val Pro Gly Pro Pro Gly Ala Val Gly Pro
                435                 440                 445
Ala Gly Lys Asp Gly Glu Ala Gly Ala Gln Gly Pro Pro Gly Pro Ala
                450                 455                 460
Gly Pro Ala Gly Glu Arg Gly Glu Gln Gly Pro Ala Gly Ser Pro Gly
465                 470                 475                 480
```

-continued

```
Phe Gln Gly Leu Pro Gly Pro Ala Gly Pro Pro Gly Glu Ala Gly Lys
                485                 490                 495

Pro Gly Glu Gln Gly Val Pro Gly Asp Leu Gly Ala Pro Gly Pro Ser
            500                 505                 510

Gly Ala Arg Gly Glu Arg Gly Phe Pro Gly Glu Arg Gly Val Gln Gly
        515                 520                 525

Pro Pro Gly Pro Ala Gly Pro Arg Gly Ala Asn Gly Ala Pro Gly Asn
    530                 535                 540

Asp Gly Ala Lys Gly Asp Ala Gly Ala Pro Gly Ala Pro Gly Ser Gln
545                 550                 555                 560

Gly Ala Pro Gly Leu Gln Gly Met Pro Gly Glu Arg Gly Ala Ala Gly
                565                 570                 575

Leu Pro Gly Pro Lys Gly Asp Arg Gly Asp Ala Gly Pro Lys Gly Ala
            580                 585                 590

Asp Gly Ser Pro Gly Lys Asp Gly Val Arg Gly Leu Thr Gly Pro Ile
        595                 600                 605

Gly Pro Pro Gly Pro Ala Gly Ala Pro Gly Asp Lys Gly Glu Ser Gly
    610                 615                 620

Pro Ser Gly Pro Ala Gly Pro Thr Gly Ala Arg Gly Ala Pro Gly Asp
625                 630                 635                 640

Arg Gly Glu Pro Gly Pro Pro Gly Pro Ala Gly Phe Ala Gly Pro Pro
                645                 650                 655

Gly Ala Asp Gly Gln Pro Gly Ala Lys Gly Glu Pro Gly Asp Ala Gly
            660                 665                 670

Ala Lys Gly Asp Ala Gly Pro Pro Gly Pro Ala Gly Pro Ala Gly Pro
        675                 680                 685

Pro Gly Pro Ile Gly Asn Val Gly Ala Pro Gly Ala Lys Gly Ala Arg
    690                 695                 700

Gly Ser Ala Gly Pro Pro Gly Ala Thr Gly Phe Pro Gly Ala Ala Gly
705                 710                 715                 720

Arg Val Gly Pro Pro Gly Pro Ser Gly Asn Ala Gly Pro Pro Gly Pro
                725                 730                 735

Pro Gly Pro Ala Gly Lys Glu Gly Gly Lys Gly Pro Arg Gly Glu Thr
            740                 745                 750

Gly Pro Ala Gly Arg Pro Gly Glu Val Gly Pro Pro Gly Pro Pro Gly
        755                 760                 765

Pro Ala Gly Glu Lys Gly Ser Pro Gly Ala Asp Gly Pro Ala Gly Ala
    770                 775                 780

Pro Gly Thr Pro Gly Pro Gln Gly Ile Ala Gly Gln Arg Gly Val Val
785                 790                 795                 800

Gly Leu Pro Gly Gln Arg Gly Glu Arg Gly Phe Pro Gly Leu Pro Gly
                805                 810                 815

Pro Ser Gly Glu Pro Gly Lys Gln Gly Pro Ser Gly Ala Ser Gly Glu
            820                 825                 830

Arg Gly Pro Pro Gly Pro Met Gly Pro Pro Gly Leu Ala Gly Pro Pro
        835                 840                 845

Gly Glu Ser Gly Arg Glu Gly Ala Pro Gly Ala Glu Gly Ser Pro Gly
    850                 855                 860

Arg Asp Gly Ser Pro Gly Ala Lys Gly Asp Arg Gly Glu Thr Gly Pro
865                 870                 875                 880

Ala Gly Pro Pro Gly Ala Pro Gly Ala Pro Gly Ala Pro Gly Pro Val
                885                 890                 895

Gly Pro Ala Gly Lys Ser Gly Asp Arg Gly Glu Thr Gly Pro Ala Gly
```

```
                        900                 905                 910
Pro Ala Gly Pro Val Gly Pro Ala Gly Ala Arg Gly Pro Ala Gly Pro
            915                 920                 925

Gln Gly Pro Arg Gly Asp Lys Gly Glu Thr Gly Glu Gln Gly Asp Arg
            930                 935                 940

Gly Ile Lys Gly His Arg Gly Phe Ser Gly Leu Gln Gly Pro Pro Gly
945                 950                 955                 960

Pro Pro Gly Ser Pro Gly Glu Gln Gly Pro Ser Gly Ala Ser Gly Pro
                965                 970                 975

Ala Gly Pro Arg Gly Pro Pro Gly Ser Ala Gly Ala Pro Gly Lys Asp
            980                 985                 990

Gly Leu Asn Gly Leu Pro Gly Pro Ile Gly Pro Pro Gly Pro Arg Gly
            995                1000                1005

Arg Thr Gly Asp Ala Gly Pro Val Gly Pro Pro Gly Pro Pro Gly Pro
        1010                1015                1020

Pro Gly Pro Pro Gly Pro Pro Ser Ala Gly Phe Asp Phe Ser Phe Leu
1025                1030                1035                1040

Pro Gln Pro Pro Gln Glu Lys Ala His Asp Gly Gly Arg Tyr Tyr Arg
            1045                1050                1055

Ala (2) INFORMATION FOR SEQ ID NO: 2:

(i) SEQUENCE CHARACTERISTICS:
        (A) LENGTH: 1024 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Homo sapiens
        (F) TISSUE TYPE: Collagen type I (xi) SEQUENCE DESCRIPTION: SEQ ID NO: 2:

Gln Tyr Asp Gly Lys Gly Val Gly Leu Gly Pro Gly Pro Met Gly Leu
1                   5                   10                  15

Met Gly Pro Arg Gly Pro Pro Gly Ala Ala Gly Ala Pro Gly Pro Gln
            20                  25                  30

Gly Phe Gln Gly Pro Ala Gly Glu Pro Gly Glu Pro Gly Gln Thr Gly
            35                  40                  45

Pro Ala Gly Ala Arg Gly Pro Ala Gly Pro Pro Gly Lys Ala Gly Glu
        50                  55                  60

Asp Gly His Pro Gly Lys Pro Gly Arg Pro Gly Glu Arg Gly Val Val
65                  70                  75                  80

Gly Pro Gln Gly Ala Arg Gly Phe Pro Gly Thr Pro Gly Leu Pro Gly
            85                  90                  95

Phe Lys Gly Ile Arg Gly His Asn Gly Leu Asp Gly Leu Lys Gly Gln
            100                 105                 110

Pro Gly Ala Pro Gly Val Lys Gly Glu Pro Gly Ala Pro Gly Glu Asn
        115                 120                 125

Gly Thr Pro Gly Gln Thr Gly Ala Arg Gly Leu Pro Gly Glu Arg Gly
        130                 135                 140

Arg Val Gly Ala Pro Gly Pro Ala Gly Ala Arg Gly Ser Asp Gly Ser
145                 150                 155                 160
```

-continued

```
Val Gly Pro Val Gly Pro Ala Gly Pro Asn Gly Ser Ala Gly Pro Pro
            165                 170                 175

Gly Phe Pro Gly Ala Pro Gly Pro Lys Gly Glu Ile Gly Ala Val Gly
            180                 185                 190

Asn Ala Gly Pro Thr Gly Pro Ala Gly Pro Arg Gly Glu Val Gly Leu
            195                 200                 205

Pro Gly Leu Ser Gly Pro Val Gly Pro Pro Gly Asn Pro Gly Ala Asn
210                 215                 220

Gly Leu Thr Gly Ala Lys Gly Ala Ala Gly Leu Pro Gly Val Ala Gly
225                 230                 235                 240

Ala Pro Gly Leu Pro Gly Pro Arg Gly Ile Pro Gly Pro Pro Gly Ala
            245                 250                 255

Ala Gly Thr Thr Gly Ala Arg Gly Leu Val Gly Glu Pro Gly Pro Ala
            260                 265                 270

Gly Ser Lys Gly Glu Ser Gly Asn Lys Gly Glu Pro Gly Ser Ala Gly
            275                 280                 285

Pro Gln Gly Pro Pro Gly Pro Ser Gly Glu Glu Gly Lys Arg Gly Pro
            290                 295                 300

Asn Gly Glu Ala Gly Ser Ala Gly Pro Pro Gly Pro Pro Gly Leu Arg
305                 310                 315                 320

Gly Ser Pro Gly Ser Arg Gly Leu Pro Gly Ala Asp Gly Arg Ala Gly
            325                 330                 335

Val Met Gly Pro Pro Gly Ser Arg Gly Ala Ser Gly Pro Ala Gly Val
            340                 345                 350

Arg Gly Pro Asn Gly Asp Ala Gly Arg Pro Gly Glu Pro Gly Leu Met
            355                 360                 365

Gly Pro Arg Gly Leu Pro Gly Ser Pro Gly Asn Ile Gly Pro Ala Gly
            370                 375                 380

Lys Glu Gly Pro Val Gly Leu Pro Gly Ile Asp Gly Arg Pro Gly Pro
385                 390                 395                 400

Ile Gly Pro Val Gly Ala Arg Gly Glu Pro Gly Asn Ile Gly Phe Pro
            405                 410                 415

Gly Pro Lys Gly Pro Thr Gly Asp Pro Gly Lys Asn Gly Asp Lys Gly
            420                 425                 430

His Ala Gly Leu Ala Gly Ala Arg Gly Ala Pro Gly Pro Asp Gly Asn
            435                 440                 445

Asn Gly Ala Gln Gly Pro Pro Gly Pro Gln Gly Val Gln Gly Gly Lys
450                 455                 460

Gly Glu Gln Gly Pro Ala Gly Pro Pro Gly Phe Gln Gly Leu Pro Gly
465                 470                 475                 480

Pro Ser Gly Pro Ala Gly Glu Val Gly Lys Pro Gly Glu Arg Gly Leu
            485                 490                 495

His Gly Glu Phe Gly Leu Pro Gly Pro Ala Gly Pro Arg Gly Glu Arg
            500                 505                 510

Gly Pro Pro Gly Glu Ser Gly Ala Ala Gly Pro Thr Gly Pro Ile Gly
            515                 520                 525

Ser Arg Gly Pro Ser Gly Pro Pro Gly Pro Asp Gly Asn Lys Gly Glu
            530                 535                 540

Pro Gly Val Val Gly Ala Val Gly Thr Ala Gly Pro Ser Gly Pro Ser
545                 550                 555                 560

Gly Leu Pro Gly Glu Arg Gly Ala Ala Gly Ile Pro Gly Gly Lys Gly
            565                 570                 575

Glu Lys Gly Glu Pro Gly Leu Arg Gly Glu Ile Gly Asn Pro Gly Arg
            580                 585                 590
```

```
Asp Gly Ala Arg Gly Ala His Gly Ala Val Gly Ala Pro Gly Pro Ala
        595                 600                 605
Gly Ala Thr Gly Asp Arg Gly Glu Ala Gly Ala Ala Gly Pro Ala Gly
        610                 615                 620
Pro Ala Gly Pro Arg Gly Ser Pro Gly Glu Arg Gly Glu Val Gly Pro
625                 630                 635                 640
Ala Gly Pro Asn Gly Phe Ala Gly Pro Ala Gly Ala Ala Gly Gln Pro
            645                 650                 655
Gly Ala Lys Gly Glu Arg Gly Gly Lys Gly Pro Lys Gly Glu Asn Gly
            660                 665                 670
Val Val Gly Pro Thr Gly Pro Val Gly Ala Ala Gly Pro Ala Gly Pro
        675                 680                 685
Asn Gly Pro Pro Gly Pro Ala Gly Ser Arg Gly Asp Gly Gly Pro Pro
        690                 695                 700
Gly Met Thr Gly Phe Pro Gly Ala Ala Gly Arg Thr Gly Pro Pro Gly
705                 710                 715                 720
Pro Ser Gly Ile Ser Gly Pro Pro Gly Pro Pro Gly Pro Ala Gly Lys
                725                 730                 735
Glu Gly Leu Arg Gly Pro Arg Gly Asp Gln Gly Pro Val Gly Arg Thr
            740                 745                 750
Gly Glu Val Gly Ala Val Gly Pro Pro Gly Phe Ala Gly Glu Lys Gly
        755                 760                 765
Pro Ser Gly Glu Ala Gly Thr Ala Gly Pro Pro Gly Thr Pro Gly Pro
770                 775                 780
Gln Gly Leu Leu Gly Ala Pro Gly Ile Leu Gly Leu Pro Gly Ser Arg
785                 790                 795                 800
Gly Glu Arg Gly Leu Pro Gly Val Ala Gly Ala Val Gly Glu Pro Gly
            805                 810                 815
Pro Leu Gly Ile Ala Gly Pro Pro Gly Ala Arg Gly Pro Pro Gly Ala
        820                 825                 830
Val Gly Ser Pro Gly Val Asn Gly Ala Pro Gly Glu Ala Gly Arg Asp
        835                 840                 845
Gly Asn Pro Gly Asn Asp Gly Pro Pro Gly Arg Asp Gly Gln Pro Gly
        850                 855                 860
His Lys Gly Glu Arg Gly Tyr Pro Gly Asn Ile Gly Pro Val Gly Ala
865                 870                 875                 880
Ala Gly Ala Pro Gly Pro His Gly Pro Val Gly Pro Ala Gly Lys His
                885                 890                 895
Gly Asn Arg Gly Glu Thr Gly Pro Ser Gly Pro Val Gly Pro Ala Gly
            900                 905                 910
Ala Val Gly Pro Arg Gly Pro Ser Gly Pro Gln Gly Ile Arg Gly Asp
        915                 920                 925
Lys Gly Glu Pro Gly Glu Lys Gly Pro Arg Gly Leu Pro Gly Phe Lys
        930                 935                 940
Gly His Asn Gly Leu Gln Gly Leu Pro Gly Ile Ala Gly His His Gly
945                 950                 955                 960
Asp Gln Gly Ala Pro Gly Ser Val Gly Pro Ala Gly Pro Arg Gly Pro
            965                 970                 975
Ala Gly Pro Ser Gly Pro Ala Gly Lys Asp Gly Arg Thr Gly His Pro
            980                 985                 990
Gly Thr Val Gly Pro Ala Gly Ile Arg Gly Pro Gln Gly His Gln Gly
        995                 1000                1005
Pro Ala Gly Pro Pro Gly Pro Pro Gly Pro Leu Gly Pro Leu Gly Val
```

|  1010 | 1015 | 1020 |

(2) INFORMATION FOR SEQ ID NO: 3:

(i) SEQUENCE CHARACTERISTICS:
        (A) LENGTH: 1060 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Homo sapiens
        (F) TISSUE TYPE: Collagen type II (xi) SEQUENCE DESCRIPTION: SEQ ID NO: 3:

```
Gln Met Ala Gly Gly Phe Asp Glu Lys Ala Gly Gly Ala Gln Leu Gly
1               5                   10                  15

Val Met Gln Gly Pro Met Gly Pro Met Gly Pro Arg Gly Pro Pro Gly
                20                  25                  30

Pro Ala Gly Ala Pro Gly Pro Gln Gly Phe Gln Gly Asn Pro Gly Glu
            35                  40                  45

Pro Gly Glu Pro Gly Val Ser Gly Pro Met Gly Pro Arg Gly Pro Pro
        50                  55                  60

Gly Pro Pro Gly Lys Pro Gly Asp Asp Gly Glu Ala Gly Lys Pro Gly
65                  70                  75                  80

Lys Ala Gly Glu Arg Gly Pro Pro Gly Pro Gln Gly Ala Arg Gly Phe
                85                  90                  95

Pro Gly Thr Pro Gly Leu Pro Gly Val Lys Gly His Arg Gly Tyr Pro
            100                 105                 110

Gly Leu Asp Gly Ala Lys Gly Glu Ala Gly Ala Pro Gly Val Lys Gly
        115                 120                 125

Glu Ser Gly Ser Pro Gly Glu Asn Gly Ser Pro Gly Pro Met Gly Pro
    130                 135                 140

Arg Gly Leu Pro Gly Glu Arg Gly Arg Thr Gly Pro Ala Gly Ala Ala
145                 150                 155                 160

Gly Ala Arg Gly Asn Asp Gly Gln Pro Gly Pro Ala Gly Pro Pro Gly
                165                 170                 175

Pro Val Gly Pro Ala Gly Gly Pro Gly Phe Pro Gly Ala Pro Gly Ala
            180                 185                 190

Lys Gly Glu Ala Gly Pro Thr Gly Ala Arg Gly Pro Glu Gly Ala Gln
        195                 200                 205

Gly Pro Arg Gly Glu Pro Gly Thr Pro Gly Ser Pro Gly Pro Ala Gly
    210                 215                 220

Ala Ser Gly Asn Pro Gly Thr Asp Gly Ile Pro Gly Ala Lys Gly Ser
225                 230                 235                 240

Ala Gly Ala Pro Gly Ile Ala Gly Ala Pro Gly Phe Pro Gly Pro Arg
                245                 250                 255

Gly Pro Pro Asp Pro Gln Gly Ala Thr Gly Pro Leu Gly Pro Lys Gly
            260                 265                 270

Gln Thr Gly Lys Pro Gly Ile Ala Gly Phe Lys Gly Glu Gln Gly Pro
        275                 280                 285

Lys Gly Glu Pro Gly Pro Ala Gly Pro Gln Gly Ala Pro Gly Pro Ala
    290                 295                 300

Gly Glu Glu Gly Lys Arg Gly Ala Arg Gly Glu Pro Gly Gly Val Gly
305                 310                 315                 320
```

-continued

```
Pro Ile Gly Pro Pro Gly Glu Arg Gly Ala Pro Gly Asn Arg Gly Phe
            325                 330                 335

Pro Gly Gln Asp Gly Leu Ala Gly Pro Lys Gly Ala Pro Gly Glu Arg
            340                 345                 350

Gly Pro Ser Gly Leu Ala Gly Pro Lys Gly Ala Asn Gly Asp Pro Gly
            355                 360                 365

Arg Pro Gly Glu Pro Gly Leu Pro Gly Ala Arg Gly Leu Thr Gly Arg
370                 375                 380

Pro Gly Asp Ala Gly Pro Gln Gly Lys Val Gly Pro Ser Gly Ala Pro
385                 390                 395                 400

Gly Glu Asp Gly Arg Pro Gly Pro Gly Pro Gln Gly Ala Arg Gly
                    405                 410                 415

Gln Pro Gly Val Met Gly Phe Pro Gly Pro Lys Gly Ala Asn Gly Glu
            420                 425                 430

Pro Gly Lys Ala Gly Glu Lys Gly Leu Pro Gly Ala Pro Gly Leu Arg
            435                 440                 445

Gly Leu Pro Gly Lys Asp Gly Glu Thr Gly Ala Glu Gly Pro Pro Gly
450                 455                 460

Pro Ala Gly Pro Ala Gly Glu Arg Gly Glu Gln Gly Ala Pro Gly Pro
465                 470                 475                 480

Ser Gly Phe Gln Gly Leu Pro Gly Pro Pro Gly Pro Pro Gly Glu Gly
            485                 490                 495

Gly Lys Pro Gly Asp Gln Gly Val Pro Gly Glu Ala Gly Ala Pro Gly
            500                 505                 510

Leu Val Gly Pro Arg Gly Glu Arg Gly Phe Pro Gly Glu Arg Gly Ser
            515                 520                 525

Pro Gly Ala Gln Gly Leu Gln Gly Pro Arg Gly Leu Pro Gly Thr Pro
530                 535                 540

Gly Thr Asp Gly Pro Lys Gly Ala Ser Gly Pro Ala Gly Pro Pro Gly
545                 550                 555                 560

Ala Gln Gly Pro Pro Gly Leu Gln Gly Met Pro Gly Glu Arg Gly Ala
            565                 570                 575

Ala Gly Ile Ala Gly Pro Lys Gly Asp Arg Gly Asp Val Gly Glu Lys
            580                 585                 590

Gly Pro Glu Gly Ala Pro Gly Lys Asp Gly Gly Arg Gly Leu Thr Gly
            595                 600                 605

Pro Ile Gly Pro Pro Gly Pro Ala Gly Ala Asn Gly Glu Lys Gly Glu
            610                 615                 620

Val Gly Pro Pro Gly Pro Ala Gly Ser Ala Gly Ala Arg Gly Ala Pro
625                 630                 635                 640

Gly Glu Arg Gly Glu Thr Gly Pro Pro Gly Thr Ser Gly Ile Ala Gly
            645                 650                 655

Pro Pro Gly Ala Asp Gly Gln Pro Gly Ala Lys Gly Glu Gln Gly Glu
            660                 665                 670

Ala Gly Gln Lys Gly Asp Ala Gly Ala Pro Gly Pro Gln Gly Pro Ser
            675                 680                 685

Gly Ala Pro Gly Pro Gln Gly Pro Thr Gly Val Thr Gly Pro Lys Gly
            690                 695                 700

Ala Arg Gly Ala Gln Gly Pro Pro Gly Ala Thr Gly Phe Pro Gly Ala
705                 710                 715                 720

Ala Gly Arg Val Gly Pro Pro Gly Ser Asn Gly Asn Pro Gly Pro Pro
            725                 730                 735

Gly Pro Pro Gly Pro Ser Gly Lys Asp Gly Pro Lys Gly Ala Arg Gly
```

```
                    740             745             750
Asp Ser Gly Pro Pro Gly Arg Ala Gly Glu Pro Gly Leu Gln Gly Pro
        755             760             765
Ala Gly Pro Pro Gly Glu Lys Gly Glu Pro Gly Asp Asp Gly Pro Ser
        770             775             780
Gly Ala Glu Gly Pro Pro Gly Pro Gln Gly Leu Ala Gly Gln Arg Gly
785             790             795             800
Ile Val Gly Leu Pro Gly Gln Arg Gly Glu Arg Gly Phe Pro Gly Leu
            805             810             815
Pro Gly Pro Ser Gly Glu Pro Gly Gln Gln Gly Ala Pro Gly Ala Ser
            820             825             830
Gly Asp Arg Gly Pro Pro Gly Pro Val Gly Pro Pro Gly Leu Thr Gly
            835             840             845
Pro Ala Gly Glu Pro Gly Arg Glu Gly Ser Pro Gly Ala Asp Gly Pro
        850             855             860
Pro Gly Arg Asp Gly Ala Ala Gly Val Lys Gly Asp Arg Gly Glu Thr
865             870             875             880
Gly Ala Val Gly Ala Pro Gly Ala Pro Gly Pro Pro Gly Ser Pro Gly
            885             890             895
Pro Ala Gly Pro Thr Gly Lys Gln Gly Asp Arg Gly Glu Ala Gly Ala
            900             905             910
Gln Gly Pro Met Gly Pro Ser Gly Pro Ala Gly Ala Arg Gly Ile Gln
            915             920             925
Gly Pro Gln Gly Pro Arg Gly Asp Lys Gly Glu Ala Gly Glu Pro Gly
        930             935             940
Glu Arg Gly Leu Lys Gly His Arg Gly Phe Thr Gly Leu Gln Gly Leu
945             950             955             960
Pro Gly Pro Pro Gly Pro Ser Gly Asp Gln Gly Ala Ser Gly Pro Ala
            965             970             975
Gly Pro Ser Gly Pro Arg Gly Pro Pro Gly Pro Val Gly Pro Ser Gly
            980             985             990
Lys Asp Gly Ala Asn Gly Ile Pro Gly Pro Ile Gly Pro Pro Gly Pro
        995             1000            1005
Arg Gly Arg Ser Gly Glu Thr Gly Pro Ala Gly Pro Pro Gly Asn Pro
    1010            1015            1020
Gly Pro Pro Gly Pro Pro Gly Pro Pro Gly Pro Gly Ile Asp Met Ser
1025            1030            1035            1040
Ala Phe Ala Gly Leu Gly Pro Arg Glu Lys Gly Pro Asp Pro Leu Gln
            1045            1050            1055
Tyr Met Arg Ala
        1060

(2) INFORMATION FOR SEQ ID NO: 4:

(i) SEQUENCE CHARACTERISTICS:
        (A) LENGTH: 1057 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Homo sapiens
        (F) TISSUE TYPE: Collagen type III (ix) FEATURE:
```

(A) NAME/KEY: Modified-site
(B) LOCATION: 1055
(D) OTHER INFORMATION: /label= Modified
    /note= "Ala may be Pro"

(xi) SEQUENCE DESCRIPTION: SEQ ID NO: 4:

```
Gln Asn Tyr Ser Pro Gln Tyr Asp Ser Tyr Asp Val Lys Ser Gly Val
 1               5                  10                  15

Ala Val Gly Gly Leu Ala Gly Tyr Pro Gly Pro Ala Gly Pro Pro Gly
             20                  25                  30

Pro Pro Gly Pro Pro Gly Thr Ser Gly His Pro Gly Ser Pro Gly Ser
         35                  40                  45

Pro Gly Tyr Gln Gly Pro Pro Gly Glu Pro Gly Gln Ala Gly Pro Ser
     50                  55                  60

Gly Pro Pro Gly Pro Pro Gly Ala Ile Gly Pro Ser Gly Pro Ala Gly
65                  70                  75                  80

Lys Asp Gly Glu Ser Gly Arg Pro Gly Arg Pro Gly Glu Arg Gly Leu
                 85                  90                  95

Pro Gly Pro Pro Gly Ile Lys Gly Pro Ala Gly Ile Pro Gly Phe Pro
             100                 105                 110

Gly Met Lys Gly His Arg Gly Phe Asp Gly Arg Asn Gly Glu Lys Gly
             115                 120                 125

Glu Thr Gly Ala Pro Gly Leu Lys Gly Glu Asn Gly Leu Pro Gly Glu
    130                 135                 140

Asn Gly Ala Pro Gly Pro Met Gly Pro Arg Gly Ala Pro Gly Glu Arg
145                 150                 155                 160

Gly Arg Pro Gly Leu Pro Gly Ala Ala Gly Ala Arg Gly Asn Asp Gly
                 165                 170                 175

Ala Arg Gly Ser Asp Gly Gln Pro Gly Pro Pro Gly Pro Pro Gly Thr
             180                 185                 190

Ala Gly Phe Pro Gly Ser Pro Gly Ala Lys Gly Glu Val Gly Pro Ala
             195                 200                 205

Gly Ser Pro Gly Ser Asn Gly Ala Pro Gly Gln Arg Gly Glu Pro Gly
             210                 215                 220

Pro Gln Gly His Ala Gly Ala Gln Gly Pro Pro Gly Pro Pro Gly Ile
225                 230                 235                 240

Asn Gly Ser Pro Gly Gly Lys Gly Glu Met Gly Pro Ala Gly Ile Pro
                 245                 250                 255

Gly Ala Pro Gly Leu Met Gly Ala Arg Gly Pro Pro Gly Pro Ala Gly
             260                 265                 270

Ala Asn Gly Ala Pro Gly Leu Arg Gly Gly Ala Gly Glu Pro Gly Lys
             275                 280                 285

Asn Gly Ala Lys Gly Glu Pro Gly Pro Arg Gly Glu Arg Gly Glu Ala
             290                 295                 300

Gly Ile Pro Gly Val Pro Gly Ala Lys Gly Glu Asp Gly Lys Asp Gly
305                 310                 315                 320

Ser Pro Gly Glu Pro Gly Ala Asn Gly Leu Pro Gly Ala Ala Gly Glu
                 325                 330                 335

Arg Gly Ala Pro Gly Phe Arg Gly Pro Ala Gly Pro Asn Gly Ile Pro
             340                 345                 350

Gly Glu Lys Gly Pro Ala Gly Glu Arg Gly Ala Pro Gly Pro Ala Gly
             355                 360                 365

Pro Arg Gly Ala Ala Gly Glu Pro Gly Arg Asp Gly Val Pro Gly Gly
             370                 375                 380

Pro Gly Met Arg Gly Met Pro Gly Ser Pro Gly Gly Pro Gly Ser Asp
```

```
                385                 390                 395                 400
Gly Lys Pro Gly Pro Gly Ser Gln Gly Glu Ser Gly Arg Pro Gly
                    405                 410                 415
Pro Pro Gly Pro Ser Gly Pro Arg Gly Gln Pro Gly Val Met Gly Phe
                    420                 425                 430
Pro Gly Pro Lys Gly Asn Asp Gly Ala Pro Gly Lys Asn Gly Glu Arg
                    435                 440                 445
Gly Gly Pro Gly Gly Pro Gly Pro Gln Gly Pro Pro Gly Lys Asn Gly
        450                 455                 460
Glu Thr Gly Pro Gln Gly Pro Pro Gly Pro Thr Gly Pro Gly Gly Asp
465                 470                 475                 480
Lys Gly Asp Thr Gly Pro Pro Gly Pro Gln Gly Leu Gln Gly Leu Pro
                    485                 490                 495
Gly Thr Gly Gly Pro Pro Gly Glu Asn Gly Lys Pro Gly Glu Pro Gly
                500                 505                 510
Pro Lys Gly Asp Ala Gly Ala Pro Gly Ala Pro Gly Lys Gly Asp
            515                 520                 525
Ala Gly Ala Pro Gly Glu Arg Gly Pro Pro Gly Leu Ala Gly Ala Pro
    530                 535                 540
Gly Leu Arg Gly Gly Ala Gly Pro Pro Gly Pro Glu Gly Gly Lys Gly
545                 550                 555                 560
Ala Ala Gly Pro Pro Gly Pro Pro Gly Ala Ala Gly Thr Pro Gly Leu
                    565                 570                 575
Gln Gly Met Pro Gly Glu Arg Gly Gly Leu Gly Ser Pro Gly Pro Lys
                580                  585                 590
Gly Asp Lys Gly Glu Pro Gly Gly Pro Gly Ala Asp Gly Val Pro Gly
            595                 600                 605
Lys Asp Gly Pro Arg Gly Pro Thr Gly Pro Ile Gly Pro Pro Gly Pro
610                 615                 620
Ala Gly Gln Pro Gly Asp Lys Gly Glu Gly Gly Ala Pro Gly Leu Pro
625                 630                 635                 640
Gly Ile Ala Gly Pro Arg Gly Ser Pro Gly Glu Arg Gly Glu Thr Gly
                    645                 650                 655
Pro Pro Gly Pro Ala Gly Phe Pro Gly Ala Pro Gly Gln Asn Gly Glu
                660                  665                 670
Pro Gly Gly Lys Gly Glu Arg Gly Ala Pro Gly Glu Lys Gly Glu Gly
            675                 680                 685
Gly Pro Pro Gly Val Ala Gly Pro Pro Gly Gly Ser Gly Pro Ala Gly
            690                 695                 700
Pro Pro Gly Pro Gln Gly Val Lys Gly Glu Arg Gly Ser Pro Gly Gly
705                 710                 715                 720
Pro Gly Ala Ala Gly Phe Pro Gly Ala Arg Gly Leu Pro Gly Pro Pro
                    725                 730                 735
Gly Ser Asn Gly Asn Pro Gly Pro Pro Gly Pro Ser Gly Ser Pro Gly
                740                 745                 750
Lys Asp Gly Pro Pro Gly Pro Ala Gly Asn Thr Gly Ala Pro Gly Ser
            755                 760                 765
Pro Gly Val Ser Gly Pro Lys Gly Asp Ala Gly Gln Pro Gly Glu Lys
        770                 775                 780
Gly Ser Pro Gly Ala Gln Gly Pro Pro Gly Ala Pro Gly Pro Leu Gly
785                 790                 795                 800
Ile Ala Gly Ile Thr Gly Ala Arg Gly Leu Ala Gly Pro Pro Gly Met
                    805                 810                 815
```

```
                Pro Gly Pro Arg Gly Ser Pro Gly Pro Gln Gly Val Lys Gly Glu Ser
                            820             825             830

Gly Lys Pro Gly Ala Asn Gly Leu Ser Gly Glu Arg Gly Pro Pro Gly
                            835             840             845

Pro Gln Gly Leu Pro Gly Leu Ala Gly Thr Ala Gly Glu Pro Gly Arg
                    850             855             860

Asp Gly Asn Pro Gly Ser Asp Gly Leu Pro Gly Arg Asp Gly Ser Pro
                865             870             875             880

Gly Gly Lys Gly Asp Arg Gly Glu Asn Gly Ser Pro Gly Ala Pro Gly
                            885             890             895

Ala Pro Gly His Pro Gly Pro Pro Gly Pro Val Gly Pro Ala Gly Lys
                            900             905             910

Ser Gly Asp Arg Gly Glu Ser Gly Pro Ala Gly Pro Ala Gly Ala Pro
                    915             920             925

Gly Pro Ala Gly Ser Arg Gly Ala Pro Gly Pro Gln Gly Pro Arg Gly
                    930             935             940

Asp Lys Gly Glu Thr Gly Glu Arg Gly Ala Ala Gly Ile Lys Gly His
                945             950             955             960

Arg Gly Phe Pro Gly Asn Pro Gly Ala Pro Gly Ser Pro Gly Pro Ala
                            965             970             975

Gly Gln Gln Gly Ala Ile Gly Ser Pro Gly Pro Ala Gly Pro Arg Gly
                            980             985             990

Pro Val Gly Pro Ser Gly Pro Pro Gly Lys Asp Gly Thr Ser Gly His
                            995            1000            1005

Pro Gly Pro Ile Gly Pro Pro Gly Pro Arg Gly Asn Arg Gly Glu Arg
                    1010            1015            1020

Gly Ser Glu Gly Ser Pro Gly His Pro Gly Gln Pro Gly Pro Pro Gly
                1025            1030            1035            1040

Pro Pro Gly Ala Pro Gly Pro Cys Cys Gly Gly Val Gly Ala Ala Ala
                                1045            1050            1055

Ile
```